United States Patent
Siddiqui

(10) Patent No.: US 11,957,924 B2
(45) Date of Patent: Apr. 16, 2024

(54) AIRWAY CARDIOVERTER-DEFIBRILLATOR SYSTEM

(71) Applicant: HAMAD MEDICAL CORPORATION, Doha (QA)

(72) Inventor: Rashid Mazhar Siddiqui, Doha (QA)

(73) Assignee: HAMAD MEDICAL CORPORATION, Doha (QA)

( * ) Notice: Subject to any disclaimer, the term of this patent is extended or adjusted under 35 U.S.C. 154(b) by 0 days.

(21) Appl. No.: 16/764,046

(22) PCT Filed: Nov. 30, 2017

(86) PCT No.: PCT/QA2017/000005
§ 371 (c)(1),
(2) Date: May 14, 2020

(87) PCT Pub. No.: WO2019/108078
PCT Pub. Date: Jun. 6, 2019

(65) Prior Publication Data
US 2020/0391042 A1    Dec. 17, 2020

(51) Int. Cl.
*A61N 1/39* (2006.01)
*A61N 1/05* (2006.01)

(52) U.S. Cl.
CPC ......... *A61N 1/3962* (2013.01); *A61N 1/0517* (2013.01); *A61N 1/0519* (2013.01); *A61N 1/3925* (2013.01)

(58) Field of Classification Search
CPC .. A61N 1/3962; A61N 1/0517; A61N 1/0519; A61N 1/3925
See application file for complete search history.

(56) References Cited

U.S. PATENT DOCUMENTS

| | | | | |
|---|---|---|---|---|
| 4,198,963 A | * | 4/1980 | Barkalow | A61M 16/0415 601/106 |
| 4,351,330 A | * | 9/1982 | Scarberry | G02B 27/01 128/207.15 |
| 4,960,133 A | * | 10/1990 | Hewson | A61N 1/0517 607/124 |
| 2002/0032468 A1 | | 3/2002 | Hill et al. | |
| 2002/0198583 A1 | * | 12/2002 | Rock | A61N 1/0517 607/122 |

(Continued)

FOREIGN PATENT DOCUMENTS

| WO | 2015/068164 A1 | 5/2015 |
|---|---|---|
| WO | 2017/052535 A1 | 3/2017 |

OTHER PUBLICATIONS

International Search Report for PCT/QA2017/000005 dated Apr. 12, 2019 [PCT/ISA/210].

(Continued)

*Primary Examiner* — Eric D. Bertram
(74) *Attorney, Agent, or Firm* — Sughrue Mion, PLLC

(57) ABSTRACT

An airway cardioverter-defibrillating system comprises a conductive Nano-balloon inserted to an airway tube. The airway cardioverter-defibrillating system functions either with unipolar or bipolar circuit configuration. The system is operatively arranged to supply safe continuous defibrillation pulses directly to the heart with simultaneous continuous external cardiac massage. The system also provides ventilation.

4 Claims, 5 Drawing Sheets

Unipolar electrically conductive balloon over an Oropharyngeal tube.

(56) References Cited

U.S. PATENT DOCUMENTS

| | | | |
|---|---|---|---|
| 2003/0120168 A1* | 6/2003 | Atlee, III | A61B 5/285 600/528 |
| 2010/0114261 A1* | 5/2010 | Errico | A61N 1/36114 607/72 |
| 2013/0146051 A1* | 6/2013 | Nolan | A61M 16/0434 128/202.16 |
| 2013/0190730 A1* | 7/2013 | Knorr | A61M 25/10 604/523 |
| 2014/0180138 A1* | 6/2014 | Freeman | A61B 5/0836 600/484 |
| 2015/0265790 A1* | 9/2015 | Nolan | A61M 16/0003 128/202.16 |
| 2018/0160939 A1* | 6/2018 | Chapman | A61M 16/201 |

OTHER PUBLICATIONS

Written Opinion for PCT/QA2017/000005 dated Apr. 12, 2019 [PCT/ISA/237].

\* cited by examiner

Schematic cross-sectional diagram of Bipolar Circuit with two halves of the electrically conductive balloon (Cathode and Anode, Orange & red colours, respectively), separated from each other by a non-conductive circumferential belt (blue colour)

Bipolar electrically conductive balloon

Bipolar electrically conductive balloon over an endotracheal tube.

Bipolar electrically conductive balloon over an Oropharyngeal tube.

Unipolar electrically conductive balloon

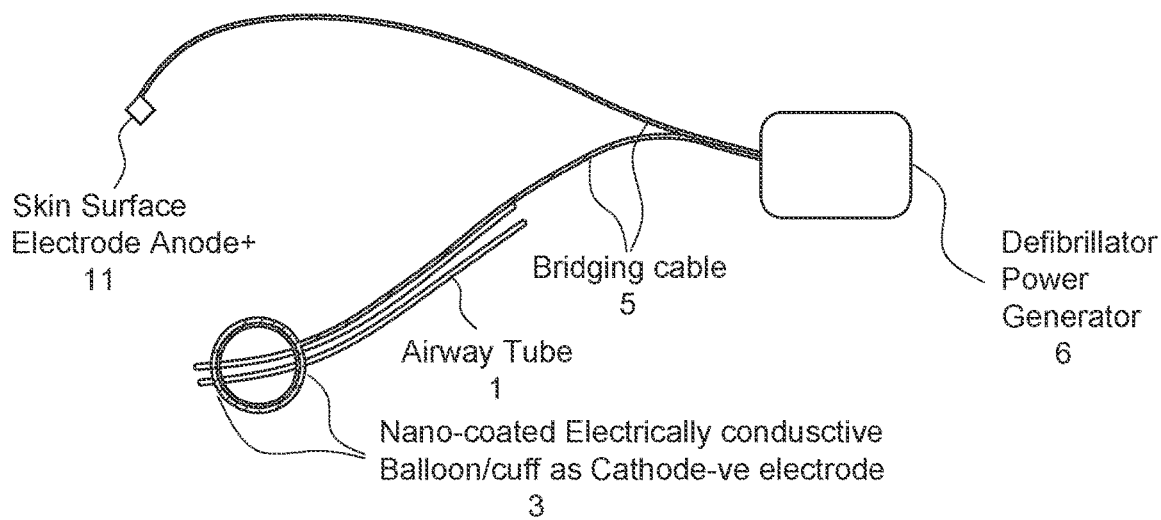

Schematic cross-sectional diagram of Unipolar Circuit where the whole circumference of the electrically conductive balloon function as a Cathode electrode (orange colour). The Anode electrode and cable (blue colour), extend from the chest wall surface to the Defibrillator power generator.

Figure 6

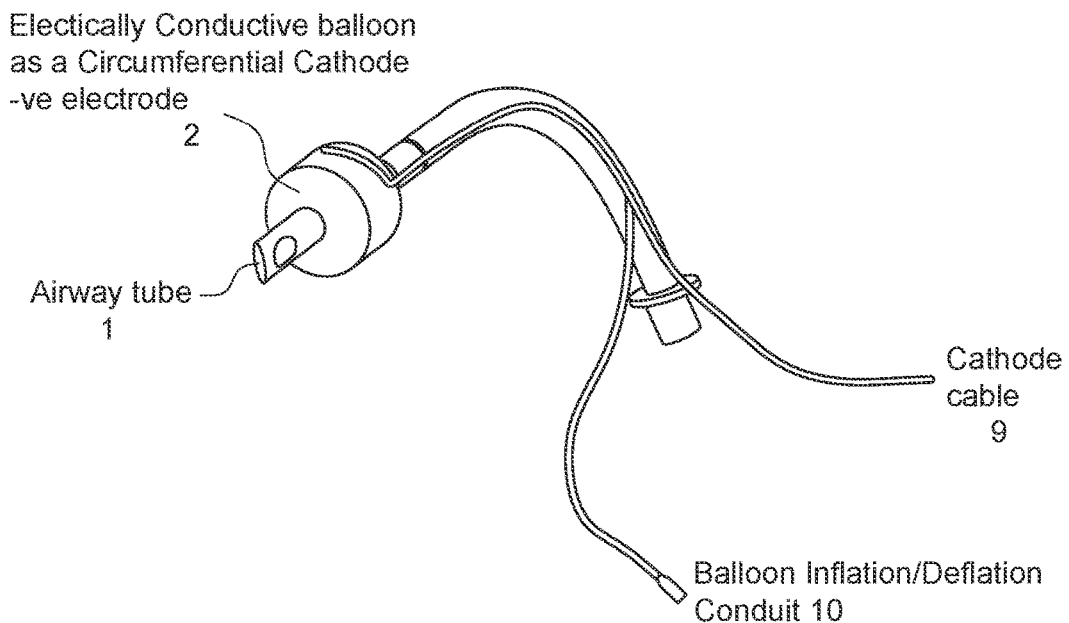

Unipolar electrically conductive balloon over an Endo-Tracheal tube.

Figure 7

Unipolar electrically conductive balloon over an Oropharyngeal tube.

Safety circuit with End Tidal capnographic sensor and circuit breaker connection

AIRWAY CARDIOVERTER-DEFIBRILLATOR SYSTEM

TECHNICAL FIELD

The present invention relates generally to a system for defibrillating a heart. More particularly for defibrillating the heart using an oro-pharyngeal path.

BACKGROUND OF THE INVENTION

Fibrillations cause the heart to stop pumping blood, leading to brain damage and/or cardiac arrest. About 10% of the ability to restart the heart is lost with every minute that the heart stays in fibrillation. Death can occur in minutes unless the normal heart rhythm is restored through defibrillation. Immediate defibrillation is crucial to the patient's survival. Defibrillators deliver a brief electric shock to the heart, which enables the heart's natural pacemaker to regain control and establish a normal heart rhythm. During defibrillation, the paddles are placed on the patient's chest, caregivers stand back, and the electric shock is delivered. The patient's pulse and heart rhythm are continually monitored. Defibrillation continues until the patient's condition stabilizes or the procedure is ordered to be discontinued. Rapid detection, CPR and defibrillation are means to restore a normal heart rhythm and prevent death after sudden cardiac arrest (SCA) due to Ventricular Fibrillation (VF). If a patient is effectively defibrillated after the onset of SCA, the survival rate becomes higher. Therefore, a way to increase the chance of survival for an SCA victim depends on early detection, CPR and defibrillation.

The surface defibrillation needs high energy defibrillating current (100 to 200 joules biphasic or 360 joules monophasic). This amount of current is very dangerous for the rescuer. Defibrillation process requires rescuers to stand aside from the patient, which necessarily interrupts the chest compression activity. Interruption of the chest compressions stops the CPR-induced blood circulation and takes several compressions before the oxygenated blood regains the previous momentum. Hence, with the external defibrillation the patient gets an inconsistent and interrupted form of circulation and oxygen delivery. However, this dangerously high defibrillating current is inevitable to deliver successful external defibrillation due to the fact, that the skin impedes nearly 90% of the current energy.

Example embodiments of the present invention aim to overcome the inconsistency between CPR circulation and oxygen delivery by defibrillating current through the airways. Airway linings are moist, non-keratinized surfaces, which pose a very low impedance to the defibrillating energy. Furthermore, large blood vessels lie in juxtaposition to the airways. As such, the blood vessels act as preferential conductor of electricity to the heart.

Thus by this invention a small amount of energy (15-20 Joules), which is harmless to the resuscitator, even when they are in contact with the patient, can be effective in defibrillating/cardioverting the patient. As a result, continuous, uninterrupted chest compression along with defibrillation may be safely performed improving the results of CPR.

SUMMARY OF THE INVENTION

The current invention is a combination of an airway tube and inflatable Nano-conductive balloon comprises defibrillating electrodes, bridging cables, and skin surface/subcutaneous electrodes. The Nano-conductive balloon/s are placed along various airway tubes, e.g. Endotracheal tube, Combitubes, King's tube, Laryngeal mask airway & Oro-pharyngeal airway. The briding cables are insulated electrical wires extending from the electrically conductive inflatable balloon/cuff to the power generator and back to the said balloon/cuff or to the skin electrodes. The aforementioned components together form a cardioverter-defibrillator system to be used in management of cardiac arrest.

BRIEF DESCRIPTION OF DRAWINGS

These and other objects and features of the present invention will be more fully disclosed or rendered obvious by the following detailed description of the preferred embodiments of the present invention, which are to be considered together with the accompanying drawings wherein like numbers refer to like elements and further wherein:

FIG. 6: Schematic cross-sectional diagram of Unipolar Circuit where the whole circumference of the electrically conductive balloon function as a Cathode electrode. The Anode electrode and cable, extend from the chest wall surface to the Defibrillator power generator.

FIG. 7: Unipolar circuit with subcutaneous skin Electrode.

DESCRIPTION OF RELATED ART

Figure 1:
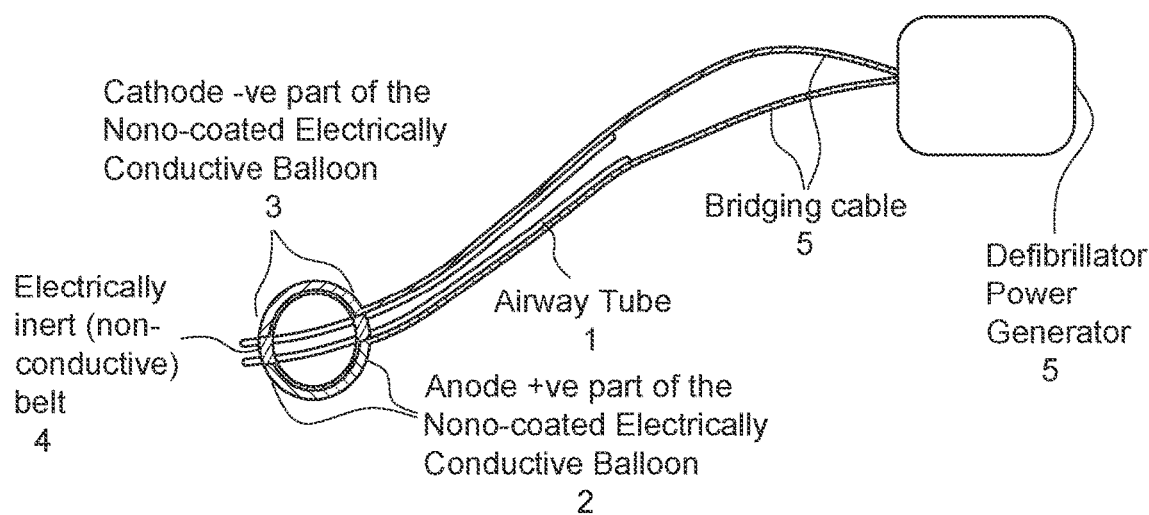
FIG. 1: Schematic cross-sectional diagram of Bipolar Circuit with two halves of the electrically conductive balloon cathode and anode separated from each other by a non-conductive circumferential belt.

The majority of cardiac arrests may be attributed to ventricular fibrillation which causes the heart to immediately stop pumping blood. Therefore, defibrillation which involves the delivery of a high energy electric shock to the thorax to depolarize the myocardium allows the perusing rhythm to restart. That is, defibrillation is administered and used to treat ventricular fibrillation. If, however, more than few minutes pass between the onset of ventricular fibrillation and the delivery of the first defibrillation shock, the heart may be so deprived of metabolic substrates that defibrillation is unsuccessful.

The role of CPR is to restore the flow of oxygenated blood to the heart, which may allow defibrillation to occur.

PRIOR ART

US application number 2017304640 described (to SATO MASASHI) describes Automated external defibrillators (AEDs) that may be used by the layperson or healthcare personnel, with basic training, by following the color indicators for the pads. These machines instruct the delivery of shocks when required or deliver them automatically. The drawbacks of this technology are that the AED systems can only be used to treat ventricular fibrillation and ventricular tachycardia and no other forms of cardiac arrhythmia. Furthermore, in order to allow the machine time to analyze the cardiac rhythm, chest compressions usually need to be stopped.

Application number WO2015039591 that described the invention is based on a selective double-lumen endotracheal tube (ETT) made of rubber/silicone or other plastic material and hence electrically nonconductive and sticking pieces of electrically conductive electrodes on the balloon with an interconnected circuit metal and wires are stuck to the balloon. The electrodes can become dislodged during insertion, or can produce injury to the inner lining of the bronchi. Therefore, the balloon may turn out to be rigid and not fully inflatable. On the other hand, the use of electrodes would generate heat and damage the tissues and/or the balloon itself, since heat generated by current is inversely related to the surface area of the electrode. Hence, the used of electrode mounted balloons may not succeed in administering defibrillation. In U.S. Pat. No. 5,417,713 (to Todd J. Cohen) Transesophageal defibrillating system transesophageal defibrillating system includes a large area anterior patch electrode and a large area posterior patch electrode, as in some conventional exterior defibrillating systems. The system is operatively arranged to supply either defibrillation pulses between the large anterior patch electrode and the distal electrode or the large posterior electrode, depending on which one of the latter two electrodes is connected or coupled by the clinician or paramedic to the defibrillating pulse source. The system includes a source of pacing pulses which may be supplied to the patient via the anterior patch electrode and at least one of the electrodes carried by the esophageal probe. The distal electrode is believed to be the more effective electrode to use for this purpose

DETAILED DESCRIPTION

Embodiments of this disclosure generally relates to medical devices and, more particularly, an airway cardioverter-defibrillator. This invention relates to a method and system for expediting the rescue of victims experiencing sudden cardiac arrest (SCA). The system, according to some embodiments, may be used in conjunction with uninterrupted external cardiac massage. The system involves an airway tube, an electrically conductive Nano-coated balloon, bridging cables and sensors. The following detailed description of example embodiments refers to the accompanying drawing. The same reference numbers in different drawings may identify the same or similar element. The drawings in detail show, for example, an airway cardioverter-defibrillator system according to some embodiments. The illustrated system comprises licensed technology Korean application number KR10-2017-0113174 "Balloon for catheter coated with multilayer electroconductive" 2,3,&4, and may be configured to receiving (sensing) and imparting (delivering) currents of biologically relevant magnitude. A high electrical conductive surface may be coated over a biocompatible balloon to form the Nano-coated balloon. The biocompatible balloon may be comprised of inflatable, flexible, foldable, and/or stretchable material. The biocompatible balloon may also be composed with high biomechanical properties such as high adhesion strength, high fracture toughness and proper biocompatibility for biomedical application. The coating over the balloon would have suitable conductive conduits/wires 5, to carry the electrical current to and from the "conductive balloon" surface. The Nano-coated balloon is capable of conducting up to 60 watts of energy, without thermal damage to the tissues or damage to the balloon due to the wide area of current transmission from the whole surface of the balloon. The Nano-coated balloon (also referred to as cuff) is completely coated and acts as one electrode while the other electrode is attached to the chest wall of the patient 4. A single conductive lead connects the single inflatable member (i.e., the balloon/cuff) to the outside of various airway tubes. For example, the airway tubes may include an endotracheal tube, Combitubes, King's tube, Laryngeal mask airway & Oropharyngeal airway. In this manner, defibrillation during Cardio-Pulmonary Resuscitation (CPR) within general wards, hospital areas, and even by emergency staff in out of the hospital places is made possible.

The illustrated embodiment further comprises the combination of an airway tube 1 and the inflatable Nano-conductive balloon 7. That is, the combination also includes the defibrillating electrodes 2,3, the electrically conductive inflatable balloon/cuff, and skin surface/subcutaneous electrodes 11. The Nano-conductive balloon/s 7 are placed along various airway tubes 1 (e.g. endotracheal tube, Combitubes, King's tube, Laryngeal mask airway & Oropharyngeal airway). Bridging cables 5 are insulated electrical wires extending from the electrically conductive inflatable balloon/cuff to the Power generator 6 and back to the cuff or to the skin electrodes 11. An electrically inert belt 4 is used to separate between the cathode 3 and the anode 2 parts of the conductive balloon. The system may also include a balloon inflation and deflation conduit 10.

One preferred embodiment of the Airway cardiac Defibrillation system as illustrated in FIG. 1 demonstrates the bipolar circuit. In the embodiment, the electrically conductive coating of the inflatable balloon/cuff 7 may comprise two or more divided separate conductive surfaces. The conducive surfaces may be referred to as electrodes and are used with a suitable widths non-conductive belt 4. Consequently, the electrodes permit the inflatable balloon/cuff to function as two or more separate cathode 3 and anode 2 electrodes. Each of these electrodes 2 and 3 may be in connection with the Defibrillator power generator unit 6.

In another embodiment, more than one electrically conductive balloons 7 could be placed along the course of the airway tube. Whereby one distal balloon acts as a cathode electrode while the proximal balloon acts as an anode electrode to complete the circuit.

Figure 5:
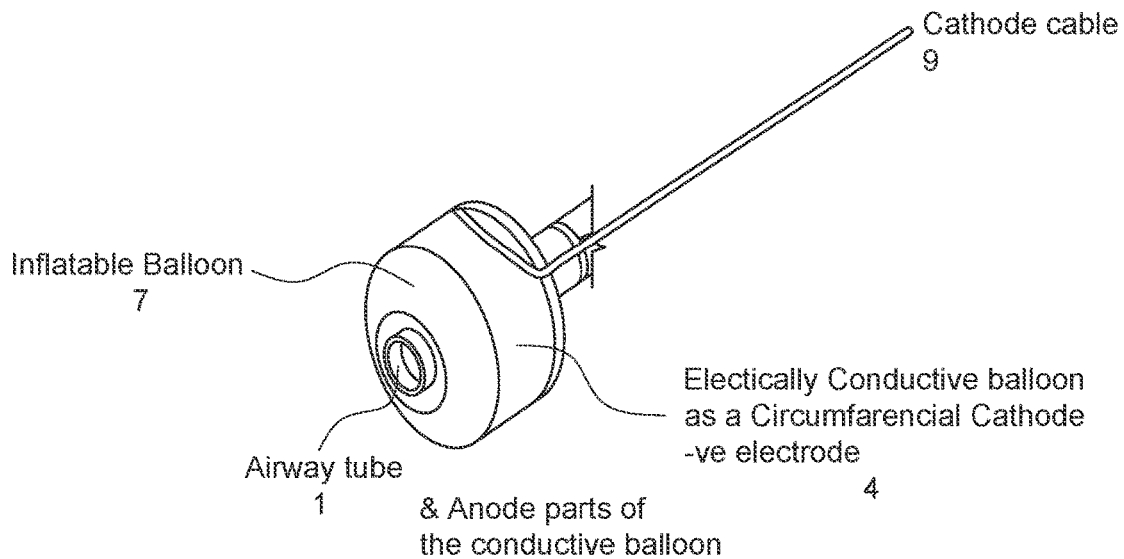
FIG. 5: Unipolar electrically conductive balloon

In another embodiment FIG. 5 clarified, the unipolar circuit of the airway defibrillator. In this embodiment, the completely electrically conductive coating of inflatable balloon/cuff, acts as a single cathode (negative terminal) electrode 3.

FIG. 6, demonstrates that one cathode bridging cable 9 extends from the electrically conductive inflatable balloon/cuff 7 to the power generator 6 and other single or multiple anode bridging cable leads 8. That is, the power generator unit 6 may supply energy via a bridge cable 5 to the surface of skin electrode 11, directly adhered to the chest wall of the person, to provide defibrillation.

Figure 8:
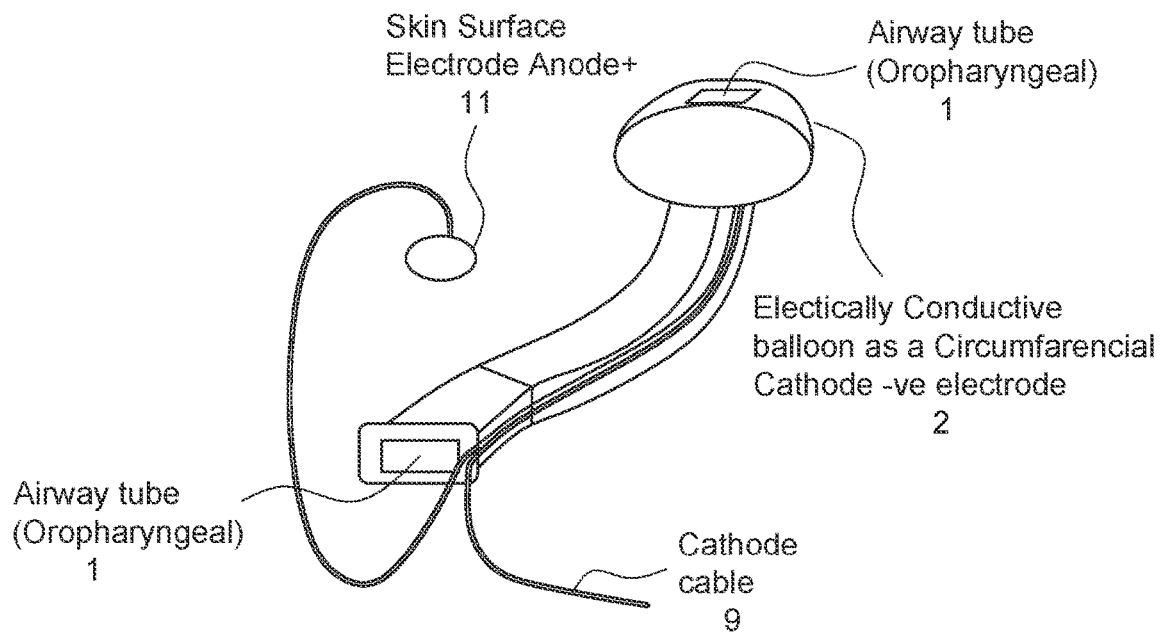
FIG. 8: Unipolar electrically conductive balloon over an endotracheal tube.
Figure 9:
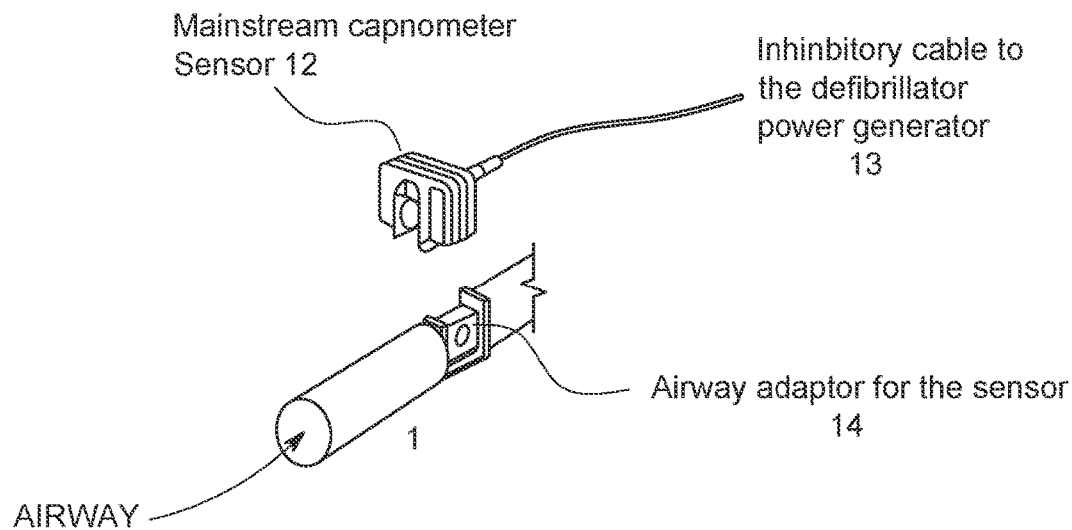
FIG. 9: Unipolar electrically conductive balloon over an Oropharyngeal tube.

FIG. 7, illustrates another embodiment of the unipolar circuitry; wherein the patient end of the external anode terminal is an un-insulated conducting segment of the cable passing through the subcutaneous tissue, by means of an attached curved or straight needle, to the skin surface. FIG. 8 illustrates such an arrangement over an endotracheal tube while FIG. 9 illustrates such an arrangement over an Oropharyngeal tube as examples for the aforementioned embodiment.

FIG. 10, shows an added safety embodiment to the airway cardioverter-defibrillator system by incorporating a breathing capnography sensor 12. The sensor functions with the appropriate electrical circuit and airway adaptor 14. That is, the sensor functions either with unipolar or bipolar circuit configuration of the airway cardioverter-defibrillator system. Additional embodiments may include activation by either mainstream &/or side stream end tidal level of carbon dioxide. That is, it sends impulse through the inhibitory cable 13 to the defibrillator power generator 6. As such, the sensor breaks the circuit off the defibrillator power generator 6 and hence stops defibrillation.

BRIEF DESCRIPTION OF DRAWINGS

These and other objects and features of the present invention will be more fully disclosed or rendered obvious by the following detailed description of the preferred embodiments of the present invention, which are to be considered together with the accompanying drawings wherein like numbers refer to like elements and further wherein:

FIG. 1: Schematic cross-sectional diagram of Bipolar Circuit with two halves of the electrically conductive balloon cathode and anode separated from each other by a non-conductive circumferential belt.

Figure 2:
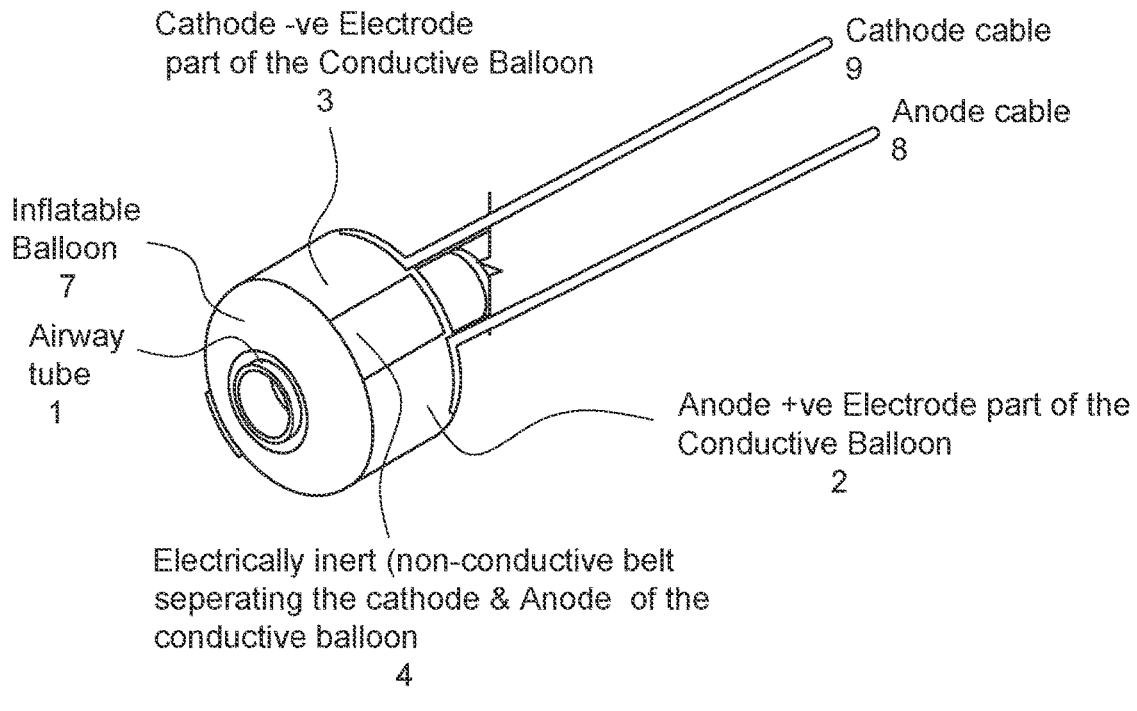
FIG. 2: Bipolar electrically conductive balloon

FIG. 2: Bipolar electrically conductive balloon

Figure 3:
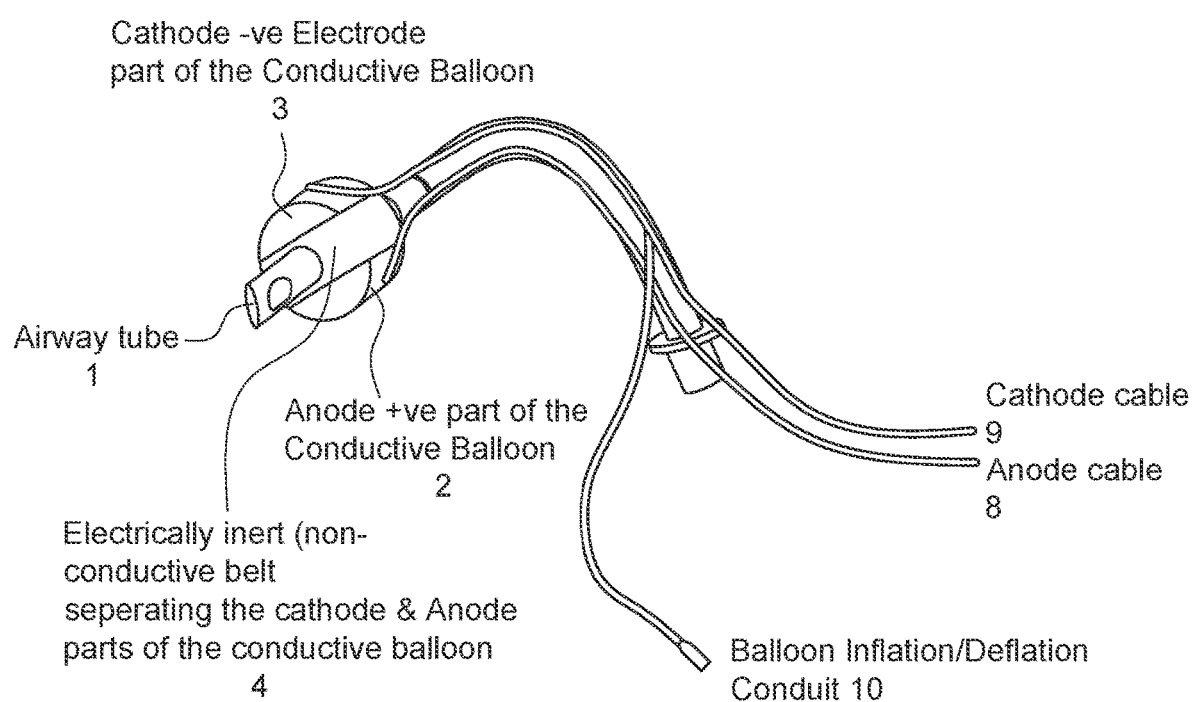
FIG. 3: Bipolar electrically conductive balloon over an endotracheal tube.

FIG. 3: Bipolar electrically conductive balloon over an endotracheal tube.

Figure 4:
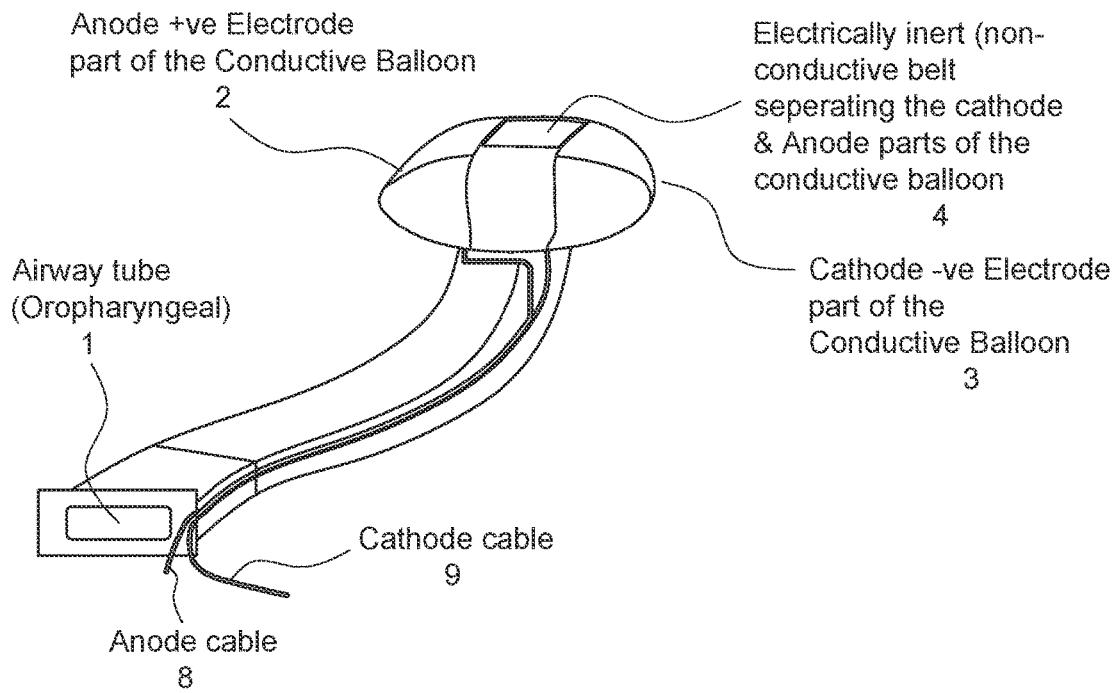
FIG. 4: Bipolar electrically conductive balloon over an Oropharyngeal tube.

FIG. 4: Bipolar electrically conductive balloon over an Oropharyngeal tube.

FIG. 5: Unipolar electrically conductive balloon

FIG. 6: Schematic cross-sectional diagram of Unipolar Circuit where the whole circumference of the electrically conductive balloon function as a Cathode electrode. The Anode electrode and cable, extend from the chest wall surface to the Defibrillator power generator.

FIG. 7: Unipolar circuit with subcutaneous skin Electrode.

FIG. 8: Unipolar electrically conductive balloon over an endotracheal tube.

FIG. 9: Unipolar electrically conductive balloon over an Oropharyngeal tube.

The invention claimed is:

1. An airway cardioverter-defibrillator system, comprising:
    an airway tube including a proximal end and a distal end wherein at least a portion of the airway tube is configured to be positioned within a trachea of the subject;
    a defibrillator power generator including at least one or more bridging cables configured to extend to at least one or more electrically conductive modules and at least one or more skin surface electrodes;
    a mainstream capnometric sensor; and
    a unipolar circuit including a whole circumference of the at least one or more electrically conductive modules to function as a cathode electrode,
    wherein the skin surface electrodes function as anode electrodes configured to adhere to a skin surface of a chest wall,
    wherein the bridging cables extend the cathode electrode and the anode electrodes to the defibrillator power generator, and
    wherein the anode electrodes are each an uninsulated conducting segment configured to attach to the skin by a curved or straight needle passing through a subcutaneous tissue.

2. The airway cardioverter-defibrillator system according to claim 1, further comprising a bipolar circuit wherein the electrically conductive module is divided into two or more separate conductive surfaces named electrodes,
    wherein the two or more separate conductive surfaces comprise suitable widths of non-conductive belts permitting the module to effectively function as two or more separate cathode and anode connected to the defibrillator power generator.

3. The airway cardioverter-defibrillator system according to claim 1, wherein two of the one or more electrically conductive modules correspond to a distal balloon acting as a cathode electrode and a proximal balloon acting as an anode electrode, and
    wherein the two of the at least one or more electrically conductive modules are placed along the airway tube to complete the unipolar circuit.

4. An airway cardioverter-defibrillator system, comprising:
    an airway tube including a proximal end and a distal end wherein at least a portion of the airway tube is configured to be positioned within the airway of the subject;
    a defibrillator power generator including at least one or more bridging cables configured to extend to an electrically conductive module and a skin surface electrode; and
    a mainstream capnometric sensor,
    a unipolar circuit including a whole circumference of the electrically conductive module to function as a cathode electrode,
    wherein the skin surface electrode functions as an external anode electrode configured to adhere to a skin surface of a chest wall, and
    wherein the external anode electrode is an uninsulated conducting segment configured to attach to the skin by a curved or straight needle passing through a subcutaneous tissue.

* * * * *